United States Patent [19]

Kurusu et al.

[11] Patent Number: 5,847,213
[45] Date of Patent: Dec. 8, 1998

[54] PROCESS FOR PRODUCTION OF TERTIARY AMINE COMPOUND

[75] Inventors: Akira Kurusu, Kyoto; Yuuji Shimasaki, Otsu, both of Japan

[73] Assignee: Nippon Shokubai Co., Ltd., Osaka, Japan

[21] Appl. No.: 807,983

[22] Filed: Mar. 3, 1997

[30] Foreign Application Priority Data

Mar. 5, 1996 [JP] Japan .................................. 8-047073

[51] Int. Cl.$^6$ ................................................. C07C 209/14
[52] U.S. Cl. .......................... 564/204; 564/215; 540/485; 544/173; 546/243; 548/543; 548/552; 548/545; 548/548
[58] Field of Search ..................................... 564/479, 488, 564/204, 215; 548/543, 552, 545, 548; 546/243; 540/485; 544/173

[56] References Cited

FOREIGN PATENT DOCUMENTS

| 0701998 | 3/1996 | European Pat. Off. . |
|---|---|---|
| 2233908 | 1/1974 | Germany . |
| 51-016657 | 2/1976 | Japan . |
| 5-279330 | 10/1993 | Japan . |
| WO9317787 | 9/1993 | WIPO . |

OTHER PUBLICATIONS

Database WPI, Section Ch, Week 9347, Derwent Publications Ltd., London, GB, (1993).

Database WPI, Section Ch, Week 7613, Derwent Publications (1976) Ltd., London, GB, (1976).

Journal Of The Chemical Society, Chemical Communications, (1995) Y. Ono et al.: "Regioselective N–alkylation of imidazoles with alcohols over zeolites".

*Primary Examiner*—Brian M. Burn
*Attorney, Agent, or Firm*—Sherman and Shalloway

[57] ABSTRACT

There is provided a process for producing a tertiary amine compound in one step without using any subsidiary raw material or any solvent, by subjecting a secondary amine compound and an alcohol to an intermolecular dehydration reaction in a gas phase. The process uses, as a catalyst, an oxide containing an alkali metal element and/or an alkaline earth metal element and silicon.

17 Claims, No Drawings

PROCESS FOR PRODUCTION OF TERTIARY AMINE COMPOUND

The present invention relates to a process for producing a tertiary amine compound by an intermolecular dehydration reaction between a secondary amine compound and an alcohol, as well as to a catalyst used in the reaction.

The tertiary amine compound produced by the process of the present invention is useful as a raw material for medicine, agricultural chemical and organic synthetic, or as a solvent.

As a general process for production of a tertiary amine compound, a process is known which comprises reacting an oxygen-containing compound (e.g. carboxylic acid, carboxylic acid ester, lactone or cyclic ether) with an alkylamine. This process, however, has problems, for example, in that the alkylamine as a raw material has high toxicity and is expensive and the reaction requires a high temperature and a high pressure.

With respect to the process for production of a tertiary amine compound by reacting a secondary amine compound with an alcohol (the process according to the present invention belongs to this process), there is described, in Japanese Patent Application Kokai (Laid-Open) No. 16657/1976, a process which comprises reacting a lactam with an alcohol in a liquid phase in the presence of a catalyst such as silica-alumina, silica-magnesia, γ-alumina, zeolite, tungstic acid, molybdic acid, metal tungstate, metal molybdate, metal vanadate, metal phosphate or the like. There is also described, in Japanese Patent Application Kokai (Laid-Open) No. 279330/1993, a process which comprises reacting a cyclic amide with an alcohol in a liquid phase in the presence of a catalyst containing a metal(s) of group VIII of periodic table. These processes, however, have problems, for example, in that since the process employs a batchwise reaction conducted at a high temperature at a high pressure, the equipment is costly and the productivity and yield are low.

With respect to the process for production of a tertiary amine compound by reacting a secondary amine compound with an alcohol in a gas phase, it is reported, in page 9 of J. Chem. Soc., Chem. Commun., 1995 that in the synthesis of an N-alkylimidazole from imidazole and an alcohol, Y type zeolite shows a high catalytic activity. The literature describes that an alkalimetal-introduced catalyst (alkali metal-exchanged zeolite) shows a low activity and an acid catalyst (acid type zeolite) shows a high activity. In the literature, no study is shown on any amine compound other than imidazole.

The objects of the present invention are to provide a simple and safe process for production of a tertiary amine compound by reacting a secondary amine compound with an alcohol in a gas phase in one step without using any subsidiary material or any solvent.

In order to alleviate the above-mentioned problems of the prior art and develop a process for producing a tertiary amine compound simply, safely and inexpensively, the present inventors made a study on a catalyst capable of allowing a secondary amine and an alcohol to give rise to an intermolecular dehydration reaction in a gas phase in one step. As a result, the present inventors found out that by using a catalyst consisting of an oxide containing an alkali metal element and/or an alkaline earth metal element and silicon, tertiary amine compound can be produced from a secondary amine compound and an alcohol at a high conversion at a high selectivity stably over a long period of time.

According to the present invention, there is provided a process for producing a tertiary amine compound represented by the following general formula (3):

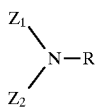

(3)

[wherein $Z_1$ and $Z_2$ are each independently an organic residue and may bond to each other to form a ring, and R is a hydrogen atom or a hydrocarbon group of 1 to 6 carbon atoms which may have a substituent(s)], which process comprises subjecting a secondary amine compound represented by the following general formula (1):

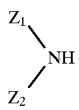

(1)

(wherein $Z_1$ and $Z_2$ have the same definitions as given above) and an alcohol represented by the following general formula (2):

$$ROH \qquad (2)$$

(wherein R has the same definition as given above) to an intermolecular dehydration reaction in a gas phase in the presence of an oxide catalyst containing an alkali metal element and/or an alkaline earth metal element and silicon.

An example of the secondary amine compound of general formula (1) is a compound represented by the following general formula (4):

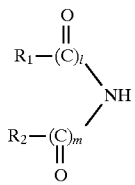

(4)

[wherein l and m are each independently 0 or 1 with a proviso that they are not 0 simultaneously; and $R_1$ and $R_2$ are each independently a hydrogen atom or a hydrocarbon group of 1 to 6 carbon atoms which may have a substituent(s), with provisos that when l is 0, $R_1$ is not a hydrogen atom and, when m is 0, $R_2$ is not a hydrogen atom].

The tertiary amine compound of general formula (3), when produced from the secondary amine compound of general formula (4) according to the present process, is a compound represented by the following general formula (5):

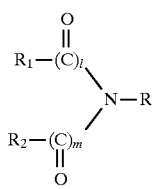

(5)

[wherein l, m, $R_1$ and $R_2$ have the same definitions as given in the general formula (4); and R has the same definition as given in the general formula (2)].

Other example of the secondary amine compound of general formula (1) is a compound represented by the following general formula (6):

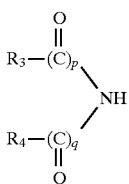

(6)

[wherein p and q are each independently 0 or 1; $R_3$ and $R_4$ are each independently a hydrocarbon group of 1–6 carbon atoms which may have a substituent(s), and may bond to each other to form a 5- to 7-membered ring together with N with provisos that the bond between $R_3$ and $R_4$ may contain a hetero atom selected from N, O and S, may contain an unsaturated bond, and may be condensed with an aromatic ring].

The tertiary amine compound of general formula (3), when produced from the secondary amine compound of general formula (6) according to the present process, is a compound represented by the following general formula (7):

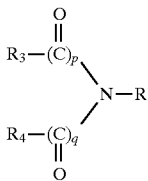

(7)

[wherein p, q, $R_3$ and $R_4$ have the same definitions as given in the general formula (6), and R has the same definition as given in the general formula (2)].

In the present process, the raw materials used need to each have such a vapor pressure that the material can be fed into the catalyst layer in a gas phase under the reaction conditions.

The secondary amine compound represented by general formula (1), which is a raw material used in the present process, is not particularly restricted as to the type. Preferable examples of the secondary amine compound are those represented by the above-mentioned general formula (4) or (6).

Specific examples of the secondary amine compound of general formula (4) include N-methylformamide, N-methylacetamide, N-methylpropylamide and N-methylacrylamide.

Specific examples of the secondary amine compound of general formula (6) include saturated cyclic amine compounds such as pyrrolidine, piperidine, hexamethyleneimine, morpholine the like; unsaturated cyclic amine compounds such as pyrroline, oxazoline, oxazolidone, thiazoline, imidazoline, oxazine, thiazine and oxathiazine and the like; aromatic cyclic amine compounds such as pyrrole, imidazole, pyrazole, triazole and the like; condensed-aromatic cyclic amine compounds such as indole, benzimidazole, benztriazole, indoline, purine, carbazole and the like; cyclic imide compounds such as succinimide, maleimide and the like; and cyclic amide compounds such as γ-butyrolactam, δ-valerolactam, ε-caprolactam, morpholinone and the like. The secondary amine compound of general formula (6) are not restricted to these. Of these compounds, cyclic imide compounds and cyclic amide compounds are particularly preferred because they can be converted to respective tertiary amine compounds very efficiently.

The alcohol represented by general formula (2), which is another raw material used in the present process, is not particularly restricted. Specific examples thereof include aliphatic alcohols such as methanol, ethanol, 1-propanol, 1-butanol, 1-hexanol and the like. Of these, methanol is particularly preferred because it is readily available, inexpensive and easy to handle.

The catalyst used in the present process is an oxide containing an alkali metal element and/or an alkaline earth metal element and silicon. It is preferably an oxide represented by the following general formula (8):

$$M_a Si_b X_c O_d \tag{8}$$

(wherein M is at least one element selected from alkali metal elements and alkaline earth metal elements; Si is silicon; X is at least one element selected from the group consisting of B, Al and P; O is oxygen; and a, b, c and d are the atom numbers of M, Si, X and O, respectively, with provisos that when a=1, b is 1–500 and c is 0–1 and d is a value determined by the values of a, b and c and the bonding states of individual constituent elements).

The proportion of silicon to M (which is at least one element selected from alkali metal elements and alkaline earth metal elements) is 1–500, preferably 5–200 in terms of atomic ratio.

The proportion of X (which is at least one element selected from the group consisting of B, Al and P) to M is generally appropriate to be 0–1 in terms of atomic ratio, although it varies depending upon the kind of M and the proportion of Si.

With respect to the alkali metal element and/or the alkaline earth metal element, which is an essential element of the present catalyst, the raw material thereof can be an oxide, a hydroxide, a halide, a salt (e.g. carbonate, nitrate, carboxylate, phosphate or sulfate), a metal or the like. With respect to silicon, which is another essential component, the raw material thereof can be silicon oxide, silicic acid, a silicic acid salt (e.g. alkali metal silicate or alkaline earth metal silicate), a silicon-containing molecular sieve (e.g. aluminosilicate or silicoaluminophosphate), an organic silicic acid ester or the like. With respect to X, which is an optional third component, the raw material thereof can be an oxide, a hydroxide, a halide, a salt (e.g. carbonate, nitrate, carboxylate, phosphate or sulfate), a metal or the like.

The catalyst of the present invention can be produced, for example, by the following processes:

(1) a process which comprises dissolving or suspending an alkali metal element source and/or an alkaline earth metal element source in water, concentrating the solution or suspension with heating and stirring, drying the concentrate, molding the dried material, and calcinating the molding;

(2) a process which comprises immersing molded silicon oxide in an aqueous solution of an alkali metal element source and/or an alkaline earth metal element source, and subjecting the resulting material to concentration with heating, drying, and calcination;

(3) a process which comprises adding, to a silicic acid salt or a silicon-containing oxide, an aqueous solution of an alkali metal element source and/or an alkaline earth metal element source, and subjecting them to mixing, drying, molding and calcination; and (4) a process which comprises doping a silicon-containing molecular sieve with an alkali metal element source and/or an alkaline earth metal element source, and subjecting the doped molecular sieve to drying, molding and calcination.

The calcination temperature employed in catalyst production is 300°–1,000° C., preferably 400°–800° C. although it varies depending upon the kinds of catalyst raw materials used.

In order to allow the catalyst to contain X (a third component), there may be used an alkali metal element source and/or an alkaline earth metal element source, at least either of which contains X, or a silicon source containing X; or, a raw material for X may be added in the course of catalyst production.

The catalyst of the present invention may be used by being supported on a known carrier (e.g. alumina or silicon carbide) or being mixed therewith.

The present catalyst has a feature that its activity is not substantially reduced even after being used in a continuous reaction over a long period of time. Even when the catalyst is deteriorated owing to the coking, etc., its activity can be restored easily by passing air through the catalyst layer for combustion of the coke.

In carrying out the present process, the reactor can be any of a fixed bed flow type and a fluidized bed type. The reaction is conducted at such a temperature and pressure that the raw materials, i.e. a secondary amine compound and an alcohol can maintain a gaseous state. The reaction pressure is ordinarily atmospheric pressure or reduced pressure, but an applied pressure may be used as well. The reaction temperature is 250°–500° C., preferably 300°–450° C., although it varies depending upon other reaction conditions. When the reaction temperature is lower than 250° C., the conversion of the secondary amine compound (a raw material) is significantly low; when the reaction temperature is higher than 500° C., the selectivity of the tertiary amine compound (an intended product) is significantly low. The proportions of the secondary amine compound and the alcohol, used in the reaction may be equimolar, or either one may be used in excess. Ordinarily, however, the alcohol is used in an amount of at least one equivalent for one equivalent of the secondary amine compound, preferably an amount 1–40 times as large as that of the secondary amine compound. In the reaction, the secondary amine compound and the alcohol are fed into the catalyst layer generally by diluting them with a substance inert to the reaction, such as nitrogen, helium, argon, hydrocarbon, ether or the like and/or reducing the pressure of the system so that the total partial pressure of the secondary amine compound and the alcohol becomes 5–600 mmHg. The alcohol may be allowed to have a role of a diluent and, in that case, it is not necessary to add any other diluent. The gas-phase space velocity (GHSV) of the total of the secondary amine compound and the alcohol is generally 1–1,000 $h^{-1}$, preferably 10–600 $h^{-1}$ although it varies depending upon the kinds of the raw materials and other reaction conditions.

The present invention is hereinafter described specifically by way of Examples. However, the present invention is in no way restricted to these Examples.

In the Examples, "conversion", "selectivity" and "per-pass yield" have the following definitions.

Conversion (mole %) =

[(moles of secondary amine compound consumed)/

(moles of secondary amine compound fed)] × 100

Selectivity (mole %) =

[(moles of tertiary amine compound formed)/

(moles of secondary amine compound consumed)] × 100

Per-pass yield (mole %) =

[(moles of tertiary amine compound formed)/

(moles of secondary amine compound fed)] × 100

EXAMPLE 1

Catalyst Production 30 g of silicon oxide was added to a solution of 4.07 g of cesium carbonate dissolved in 40 g of water. The mixture was heated on a hot water bath with stirring, to concentrate to dryness. The concentrate was subjected to drying in air at 120° C. for 20 hours, grinding to 9–16 mesh, and calcination in air at 500° C. for 2 hours, whereby was produced a catalyst having a composition of $Cs_1Si_{20}$ in terms of atomic ratio when oxygen was excluded.

Reaction 10 ml of the catalyst was filled in a stainless steel-made reaction tube having an inner diameter of 10 mm. The reaction tube was immersed in a molten salt bath of 370° C. There was used, as a raw material gas, a 2-pyrrolidone/methanol mixed gas diluted with nitrogen so that the partial pressures of 2-pyrrolidone and methanol became each 38 mmHg. This raw material gas was fed into the reaction tube at atmospheric pressure at such a velocity that the total GHSV of 2-pyrrolidone and methanol became 200 $h^{-1}$. After 1 hour from the start of the feeding, the reaction product was analyzed by gas chromatography. As a result, the conversion of 2-pyrrolidone and the selectivity and per-pass yield of N-methyl-2-pyrrolidone were 26 mole %, 100 mole % and 26 mole %, respectively. When the reaction temperature was increased to 430° C., the conversion of 2-pyrrolidone and the selectivity and per-pass yield of N-methyl-2-pyrrolidone were 59 mole %, 99 mole % and 58 mole %, respectively.

EXAMPLE 2

Reaction

A reaction was conducted in the same manner as in Example 1 except that ethanol was used in place of methanol, the partial pressures of 2-pyrrolidone and ethanol were 38 mmHg and 114 mmHg, respectively, and the total GHSV of 2-pyrrolidone and ethanol was 400 $h^{-1}$. When the reaction temperature was 430° C., after 1 hour from the start of feeding, the conversion of 2-pyrrolidone and the selectivity and per-pass yield of N-ethyl-2-pyrrolidone were 5 mole %, 100 mole % and 5 mole %, respectively.

EXAMPLE 3

Catalyst Production 30 g of silicon oxide was added to a solution of 1.69 g of potassium nitrate dissolved in 40 g of water. The mixture was heated on a hot water bath with stirring, to concentrate to dryness. The concentrate was subjected to drying in air at 120° C. for 20 hours, grinding to 9–16 mesh, and calcination in air at 600° C. for 2 hours, whereby was produced a catalyst having a composition of $K_1Si_{10}$ in terms of atomic ratio when oxygen was excluded.

Reaction

Using the above catalyst, a reaction was conducted in the same manner as in Example 1 except that the reaction temperature was changed to 400° C. After 1 hour from the start of feeding, the conversion of 2-pyrrolidone and the selectivity and per-pass yield of N-methyl-2-pyrrolidone were 38 mole %, 97 mole % and 37 mole %, respectively.

EXAMPLE 4

Catalyst Production 30 g of a spherical silica gel (5–10 mesh) was immersed in a solution of 0.67 g of sodium hydroxide dissolved in 40 g of water, for 2 hours. The resulting material was concentrated to dryness on a hot water bath. The concentrate was subjected to drying in air at 120° C. for 20 hours and calcination in air at 600° C. for 2 hours, whereby was produced a catalyst having a composition of $Na_1Si_{30}$ in terms of atomic ratio when oxygen was excluded.

Reaction

Using the above catalyst, a reaction was conducted in the same manner as in Example 1 except that succinimide was used in place of 2-pyrrolidone, the partial pressures of succinimide and methanol were 7 mmHg and 221 mmHg, respectively, and the total GHSV of succinimide and methanol was 600 $h^{-1}$ When the reaction temperature was 330° C., after 1 hour from the start of feeding, the conversion of succinimide and the selectivity and per-pass yield of N-methyl-succinimide were 63 mole %, 93 mole % and 59 mole %, respectively.

EXAMPLE 5

Reaction

A reaction was conducted in the same manner as in Example 4 except that the catalyst of Example 1 was used and the reaction temperature was changed. When the reaction temperature was 300° C., after 1 hour from the start of feeding, the conversion of succinimide and the selectivity and per-pass yield of N-methyl-succinimide were 92 mole %, 91 mole % and 84 mole %, respectively. When the reaction temperature was increased to 340° C., the conversion of succinimide and the selectivity and per-pass yield of N-methyl-succinimide were 100 mole %, 99 mole % and 99 mole %, respectively.

EXAMPLE 6

Reaction

A reaction was conducted in the same manner as in Example 1 except that maleimide was used in place of 2-pyrrolidone, the partial pressures of maleimide and methanol were 21 mmHg and 207 mmHg, respectively, and the total GHSV of maleimide and methanol was 600 $h^{-1}$. When the reaction temperature was 300° C., after 1 hour from the start of feeding, the conversion of maleimide and the selectivity and per-pass yield of N-methyl-maleimide were 100 mole %, 80 mole % and 80 mole %, respectively.

EXAMPLE 7

Catalyst Production

By using the same procedure as in Example 3 except that 1.69 g of potassium nitrate was changed to 5.13 g of rubidium hydroxide, there was produced a catalyst having a composition of $Rb_1Si_{10}$ in terms of atomic ratio when oxygen was excluded.

Reaction

Using the above catalyst, a reaction was conducted in the same manner as in Example 1 except that imidazole was used in place of 2-pyrrolidone, the partial pressures of imidazole and methanol were 26 mmHg and 50 mmHg, respectively, and the total GHSV of imidazole and methanol was 200 $h^-$. When the reaction temperature was 370° C., after 1 hour from the start of feeding, the conversion of imidazole and the selectivity and per-pass yield of N-methyl-imidazole were 57 mole %, 100 mole % and 57 mole %, respectively. When the reaction temperature was increased to 430° C., the conversion of imidazole and the selectivity and per-pass yield of N-methyl-imidazole were 85 mole %, 99 mole % and 84 mole %, respectively.

EXAMPLE 8

Reaction

A reaction was conducted in the same manner as in Example 7 except that the catalyst was changed to that of Example 1 and the reaction temperature was changed. When the reaction temperature was 400° C., after 1 hour from the start of feeding, the conversion of imidazole and the selectivity and per-pass yield of N-methyl-imidazole were 78 mole %, 100 mole % and 78 mole %, respectively. When the reaction temperature was increased to 430° C., the conversion of imidazole and the selectivity and per-pass yield of N-methyl-imidazole were 85 mole %, 100 mole % and 85 mole %, respectively.

As is demonstrated by the above Examples, by using the process and catalyst according to the present invention, a tertiary amine compound can be produced stably over a long period of time by a one-step, gas-phase intermolecular dehydration reaction of a secondary amine compound and an alcohol, without using any auxiliary raw material or any solvent.

What is claimed is:

1. A process for producing a tertiary amine compound represented by the following general formula (3):

wherein $Z_1$ and $Z_2$ are each independently an organic residue and may bond to each other to form a ring, and R is a hydrocarbon group of 1 to 6 carbon atoms which may have a substituent(s), which process comprises subjecting a secondary amine compound represented by the following general formula (1):

wherein $Z_1$ and $Z_2$ have the same definitions as given above and an alcohol represented by the following general formula (2):

wherein R has the same definition as given above to an intermolecular dehydration reaction in a gas phase in the presence of an oxide catalyst containing an alkali metal element and/or an alkaline earth metal element and silicon.

2. A process according to claim 1, wherein the secondary amine compound is a compound represented by the following general formula (4):

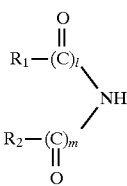

(4)

wherein l and m are each independently 0 or 1 with a proviso that they are not 0 simultaneously; and $R_1$ and $R_2$ are each independently a hydrogen atom or a hydrocarbon group of 1 to 6 carbon atoms which may have a substituent(s), with provisos that when l is 0, $R_1$ is not a hydrogen atom and, when m is 0, $R_2$ is not a hydrogen atom, and the tertiary amine compound is a compound represented by the following general formula (5):

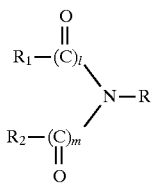

(5)

wherein l, m, $R_1$ and $R_2$ have the same definitions as given in the general formula (4), and R has the same definitions given in the general formula (2).

3. A process according to claim 1, wherein the secondary amine compound is a compound represented by the following general formula (6):

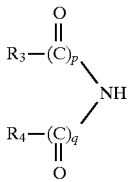

(6)

wherein p and q are each independently 0 or 1; $R_3$ and $R_4$ are each independently a hydrocarbon group of 1–6 carbon atoms which may have a substituent(s), and may bond to each other to form a 5- to 7-membered ring together with N with the provisos that the bond between $R_3$ and $R_4$ may contain a hetro atom selected from the group consisting of N, O, and S, may contain an unsaturated bond, and may be condensed with an aromatic ring, and the tertiary amine compound is a compound represented by the following general formula (7):

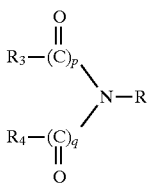

(7)

wherein p, q, $R_3$ and $R_4$ have the same definitions as given in the general formula (6), and R has the same definition as given in the general formula (2).

4. A process according to claim 1, wherein the catalyst is an oxide represented by the following general formula (8):

$$M_aSi_bX_cO_d \quad (8)$$

wherein M is at least one element selected from the group consisting of alkali metal elements and alkaline earth metal elements; Si is silicon; X is at least one element selected from the group consisting of B, Al and P; O is oxygen; and a, b, c and d are the atom numbers of M, Si, X and O, respectively, with provisos that when a=1, b is 1–500 and c is 0–1 and d is a value determined by the values of a, b and c and the bonding states of individual constituent elements.

5. A process for producing a tertiary amine compound represented by the following general formula (3):

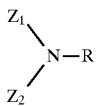

(3)

wherein $Z_1$ and $Z_2$ are each independently an organic residue and may bond to each other to form a ring, and R is a hydrocarbon group of 1 to 6 carbon atoms which may have a substituent(s), which process comprises subjecting a secondary amine compound represented by the following general formula (1):

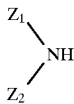

(1)

wherein $Z_1$ and $Z_2$ have the same definitions as given above and an alcohol represented by the following general formula (2):

$$ROH \quad (2)$$

wherein R has the same definition as given above to an intermolecular dehydration reaction in a gas phase at a temperature of 250° to 500° C.

in the presence of an oxide catalyst which consists essentially of an oxide represented by the following general formula (8):

$$M_aSi_bX_cO_d \quad (8)$$

wherein M is at least one element selected from the group consisting of alkali metal elements and alkaline earth metal elements; Si is silicon; X is at least one element selected from the group consisting of B, Al and P; O is oxygen; and a, b, c and d are the atom numbers of M, Si, X and O, respectively, with provisos that when a=1, b is 5–200 and c is 0–1 and d is a value determined by the values of a, b and c and the bonding states of individual constituent elements.

6. A process according to claim 5, wherein the secondary amine compound is a compound represented by the following general formula (4):

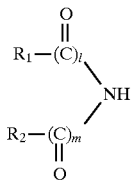

(4)

wherein l and m are each independently 0 or 1 with a proviso that they are not 0 simultaneously; and $R_1$ and $R_2$ are each independently a hydrogen atom or a hydrocarbon group of 1 to 6 carbon atoms which may have a substituent(s), with provisos that when l is 0, $R_1$ is not a hydrogen atom and, when m is 0, $R_2$ is not a hydrogen atom, and the tertiary amine compound is a compound represented by the following general formula (5):

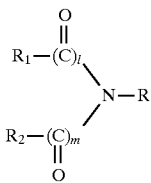
(5)

wherein l, m, $R_1$ and $R_2$ have the same definitions as given in the general formula (4), and R has the same definitions given in the general formula (2).

7. A process according to claim 5, wherein the secondary amine compound is a compound represented by the following general formula (6):

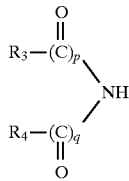
(6)

wherein p and q are each independently 0 or 1; $R_3$ and $R_4$ are each independently a hydrocarbon group of 1–6 carbon atoms which may have a substituent(s), and may bond to each other to form a 5- to 7-membered ring together with N with the provisos that the bond between $R_3$ and $R_4$ may contain a hetro atom selected from the group consisting of N, O, and S, may contain an unsaturated bond, and may be condensed with an aromatic ring, and the tertiary amine compound is a compound represented by the following general formula (7):

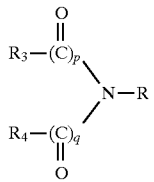
(7)

wherein p, q, $R_3$ and $R_4$ have the same definitions as given in the general formula (6), and R has the same definition as given in the general formula (2).

8. A process for producing a tertiary amine compound represented by the following general formula (5):

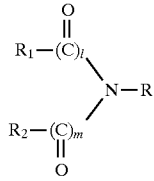
(5)

wherein l, m, $R_1$ and $R_2$ have the same definitions as given below in the general formula (4), and R is a hydrocarbon group of 1 to 6 carbon atoms which may have a substituent (s), which process comprises subjecting a secondary amine compound represented by the following formula (4):

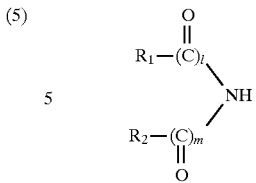
(4)

wherein l and m are each independently 0 or 1 with a proviso that they are not 0 simultaneously; and $R_1$ and $R_2$ are each independently a hydrogen atom or a hydrocarbon group of 1 to 6 carbon atoms which may have a substituent(s), with provisos that when l is 0, $R_1$ is not a hydrogen atom and, when m is 0, $R_2$ is not a hydrogen atom and an alcohol represented by the following general formula (2):

ROH (2)

wherein R has the same definition as given above to an intermolecular dehydration reaction in a gas phase at a temperature of 300° to 450° C.

in the presence of an oxide catalyst which consists essentially of formula (8):

$$M_aSi_bX_cO_d \quad (8)$$

wherein M is at least one element selected from the group consisting of alkali metal elements and alkaline earth metal elements; Si is silicon; X is at least one element selected from the group consisting of B, Al and P; O is oxygen; and a, b, c and d are the atom numbers of M, Si, X and O, respectively, with provisos that when a=1, b is 5–200 and c is 0–1 and d is a value determined by the values of a, b and c and the bonding states of individual constituent elements.

9. The process according to claim 8, wherein the secondary amine is a member selected from the group consisting of N-methylformamide, N-methylacetamide, N-methylpropylamide and N-methylacrylamide.

10. The process according to claim 8, wherein the alcohol is a member selected from the group consisting of methanol and ethanol.

11. The process according to claim 8, wherein the oxide catalyst is a member selected from the group consisting of $Cs_1Si_{20}$, $K_1Si_{10}$, $Na_1Si_{30}$ and $Rb_1Si_{10}$.

12. A process for producing a tertiary amine compound represented by the following general formula (7):

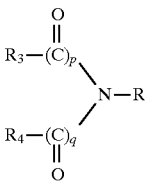
(7)

wherein p, q, $R_3$ and $R_4$ have the same definitions as given below in the general formula (6), and R is a hydrocarbon group of 1 to 6 carbon atoms which may have substituent(s), which process comprises subjecting a secondary amine compound represented by the following formula (6):

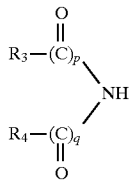

(6)

wherein p and q are each independently 0 or 1; $R_3$ and $R_4$ are each a hydrocarbon group of 1–6 carbon atoms which may have a substituent(s), and may bond to each other to form a 5- to 7-membered ring together with N with the provisos that the bond between $R_3$ and $R_4$ may contain a hetro atom selected from the group consisting of N, O, and S, may contain an unsaturated bond, and may be condensed with an aromatic ring and an alcohol represented by the following general formula (2):

ROH wherein R has the same definition as given above to an intermolecular dehydration reaction in a gas phase at a temperature of 300° to 450° C.

in the presence of an oxide catalyst which consists essentially of an oxide represented by the following general formula (8):

$$M_a Si_b X_c O_d \qquad (8)$$

wherein M is at least one element selected from the group consisting of alkali metal elements and alkaline earth metal elements; Si is silicon; X is at least one element selected from the group consisting of B, Al and P; O is oxygen; and a, b, c and d are the atom numbers of M, Si, X and O, respectively, with provisos that when a=1, b is 5–200 and c is 0–1 and d is a value determined by the values of a, b and c and the bonding states of individual constituent elements.

13. The process according to claim 12, wherein the secondary amine is a member selected from the group consisting of succinimide and maleimide.

14. The process according to claim 12, wherein the secondary amine is a member selected from the group consisting of γ-butyrolactam, δ-valerolactam, ε-caprolactam and morpholinone.

15. The process according to claim 12, wherein the alcohol is a member selected from the group consisting of methanol and ethanol.

16. The process according to claim 12, wherein the oxide catalyst is a member selected from the group consisting of $Cs_1Si_{20}K_1Si_{10}$, $Na_1Si_{30}$ and $Rb_1Si_{10}$.

17. The process according to claim 12, wherein the secondary amine is a member selected from the group consisting of 2-pyrrolidene, succinimide, maleimide and imadazole, the alcohol is a member selected from the group consisting of methanol and ethanol and the oxide catalyst is a member selected from the group consisting of $Cs_1Si_{20}$, $K_1Si_{10}$, $Na_1Si_{30}$ and $Rb_1Si_{10}$.

* * * * *